(12) United States Patent
Ahmed

(10) Patent No.: US 9,008,781 B2
(45) Date of Patent: Apr. 14, 2015

(54) METHOD AND SYSTEM FOR TREATMENT OF MOBILITY DYSFUNCTION

(71) Applicant: Zaghloul Ahmed, Staten Island, NY (US)

(72) Inventor: Zaghloul Ahmed, Staten Island, NY (US)

(73) Assignee: The Research Foundation of the City University of New York, New York, NY (US)

( * ) Notice: Subject to any disclaimer, the term of this patent is extended or adjusted under 35 U.S.C. 154(b) by 0 days.

(21) Appl. No.: 14/201,408

(22) Filed: Mar. 7, 2014

(65) Prior Publication Data

US 2014/0200387 A1    Jul. 17, 2014

Related U.S. Application Data

(63) Continuation-in-part of application No. 13/503,216, filed as application No. PCT/US2010/053720 on Oct. 22, 2010, application No. 14/201,408, which is a continuation-in-part of application No. 14/157,689, (Continued)

(51) Int. Cl.
*A61N 1/18* (2006.01)
*A61N 2/00* (2006.01)
*A61N 1/04* (2006.01)

(52) U.S. Cl.
CPC . *A61N 2/002* (2013.01); *A61N 1/04* (2013.01)

(58) Field of Classification Search
None
See application file for complete search history.

(56) References Cited

U.S. PATENT DOCUMENTS

| 5,047,005 | A | 9/1991 | Cadwell |
| 5,100,373 | A | 3/1992 | Liboff et al. |
| 5,224,922 | A | 7/1993 | Kurtz |
| 5,450,859 | A | 9/1995 | Litovitz |
| 5,562,718 | A | 10/1996 | Palermo |
| 5,738,625 | A | 4/1998 | Gluck |
| 6,263,226 | B1 * | 7/2001 | Axelgaard et al. ............ 600/391 |

(Continued)

FOREIGN PATENT DOCUMENTS

| WO | 2011050255 A2 | 4/2011 |
| WO | 2011119251 A2 | 9/2011 |
| WO | 2012054587 A2 | 4/2012 |

OTHER PUBLICATIONS

Agrawal, S. K. et al. Mechanisms of secondary injury to spinal cord axons in vitro: role of Na+, Na(+)-K(+)-ATPase, the Na(+)-H+ exchanger, and the Na(+)-Ca2+ exchanger. J. of Neuroscience 16(2): 545-552, 1996.

(Continued)

*Primary Examiner* — Brian T Gedeon
*Assistant Examiner* — Ankit Tejani
(74) *Attorney, Agent, or Firm* — Burns & Levinson LLP; Orlando Lopez

(57) ABSTRACT

Effective systems and methods for improving neural communication impairment of a vertebrate being and affecting motor activity of a peripheral body part including a first signal providing component configured to provide pulsed peripheral stimulation signals at the peripheral body part, a second signal providing component configured to provide a pulsed motor cortex stimulation signal to a motor cortex area, a substantially DC signal providing component configured to provide direct current spinal stimulation signal at a neural spinal junction and a controller component configured to control timing of the pulsed peripheral stimulation signals and the pulsed motor cortex stimulation signal.

16 Claims, 16 Drawing Sheets

Related U.S. Application Data filed on Jan. 17, 2014, which is a continuation of application No. 13/635,929, filed as application No. PCT/US2011/022283 on Jan. 24, 2011, now abandoned.

(60) Provisional application No. 61/774,207, filed on Mar. 7, 2013, provisional application No. 61/780,924, filed on Mar. 13, 2013, provisional application No. 61/253,948, filed on Oct. 22, 2009, provisional application No. 61/316,319, filed on Mar. 22, 2010.

(56) References Cited

U.S. PATENT DOCUMENTS

| | | |
|---|---|---|
| 7,160,241 B1 | 1/2007 | Herbst |
| 7,660,631 B2 | 2/2010 | Whitehurst et al. |
| 7,758,490 B2 | 7/2010 | Pilla et al. |
| 2002/0161415 A1 | 10/2002 | Cohen et al. |
| 2003/0171640 A1 | 9/2003 | Canedo |
| 2003/0217754 A1 | 11/2003 | Thomas et al. |
| 2004/0172097 A1 | 9/2004 | Brodard et al. |
| 2005/0137648 A1 | 6/2005 | Cosendai et al. |
| 2006/0041283 A1 | 2/2006 | Gelfand et al. |
| 2006/0052657 A9 | 3/2006 | Zabara |
| 2006/0116720 A1 | 6/2006 | Knoblich |
| 2008/0004484 A1 | 1/2008 | Wieraszko et al. |
| 2008/0058878 A1* | 3/2008 | King .................................. 607/5 |
| 2008/0208287 A1 | 8/2008 | Palermo et al. |
| 2009/0177112 A1* | 7/2009 | Gharib et al. .................. 600/554 |
| 2009/0204175 A1 | 8/2009 | Zanella et al. |
| 2011/0224753 A1 | 9/2011 | Palermo et al. |
| 2012/0041498 A1 | 2/2012 | Gliner et al. |
| 2013/0035745 A1 | 2/2013 | Ahmed et al. |

OTHER PUBLICATIONS

Laycock, D.C. Pulse Magnetic Field Therapy and the Physiotherapist, http://www.tgselectronics.com.au/physio.html, Jul. 1997.

Wieraszko, A. Dantrolene Modulates the Influence of Steady Magnetic Fields on Hippocampal Evoked Potentials in Vitro, Bioelectromagnetics 21:175-182 (2000).

International Search Report and Written Opinion dated Jun. 23, 2014 for International Application No. PCT/US14/21889.

* cited by examiner

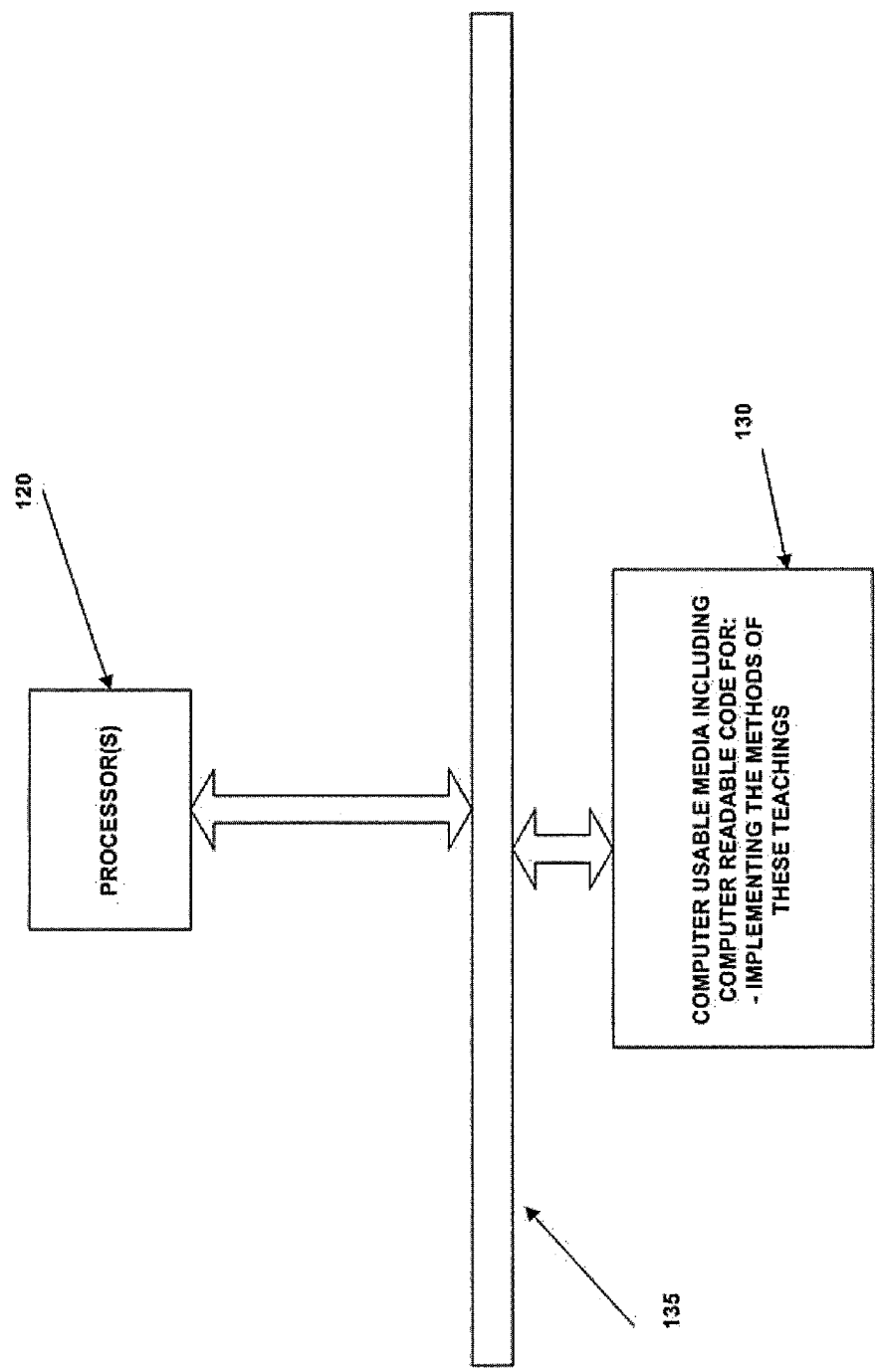

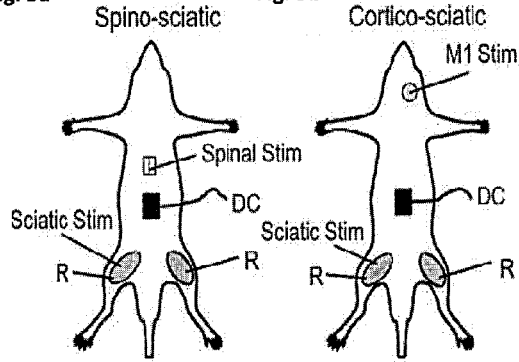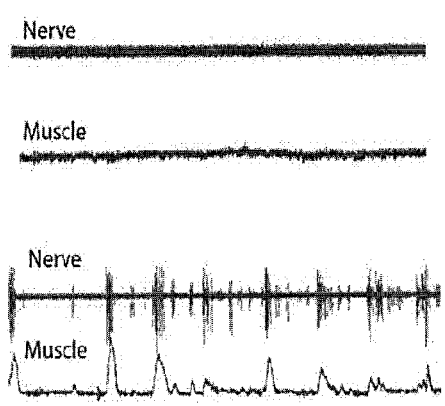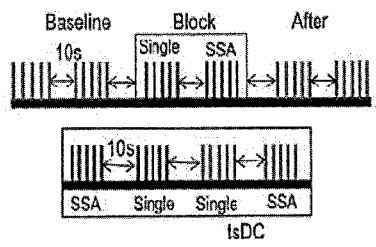

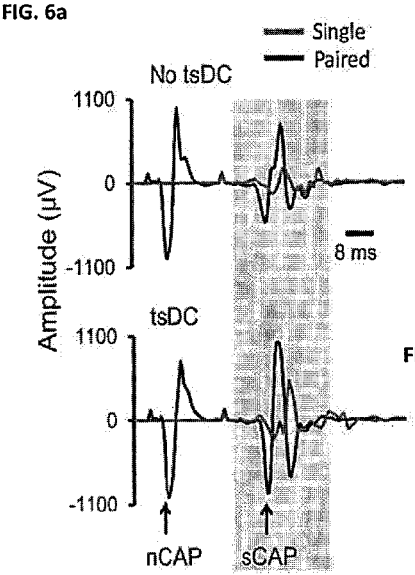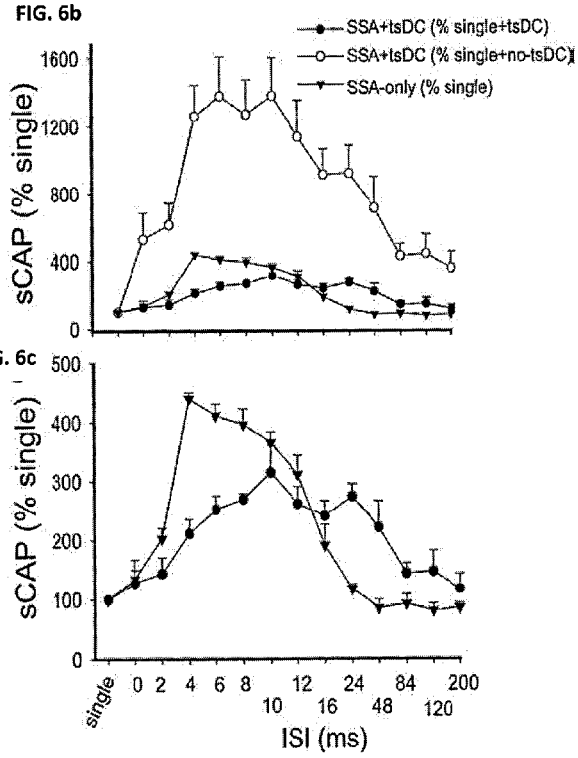

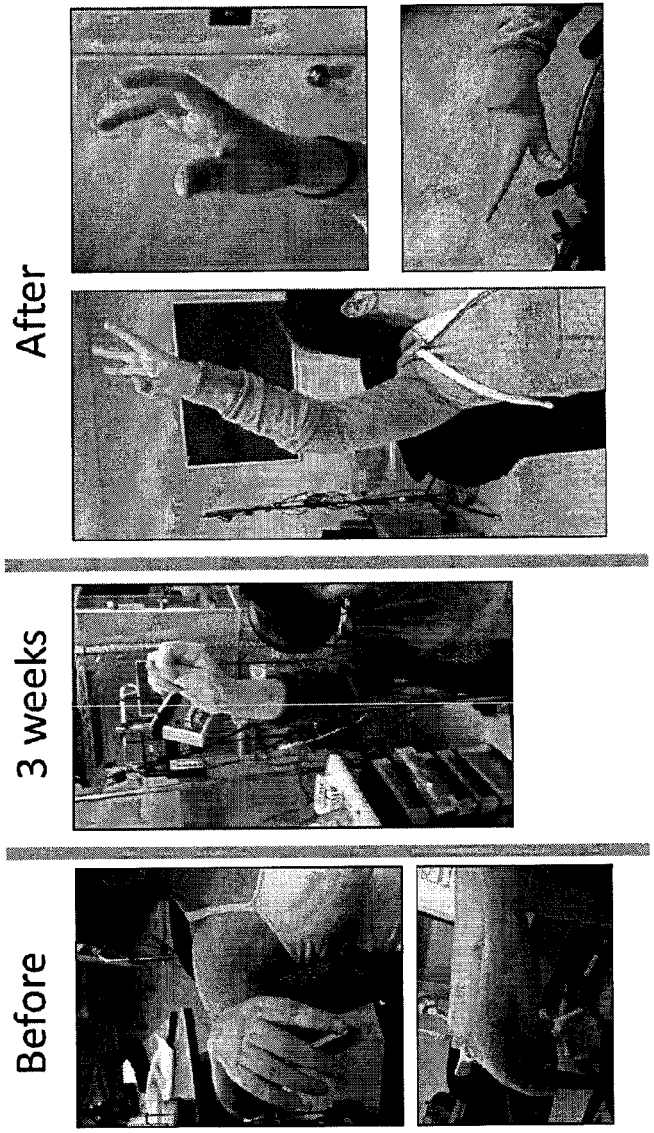

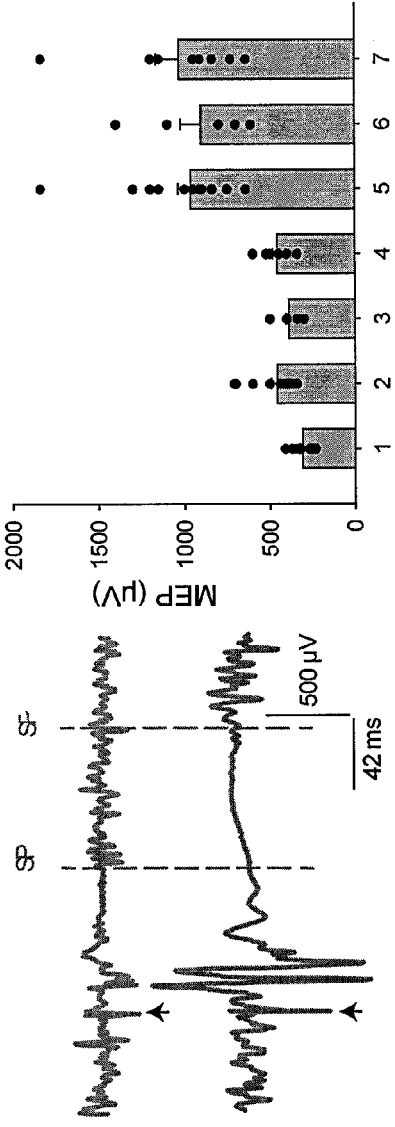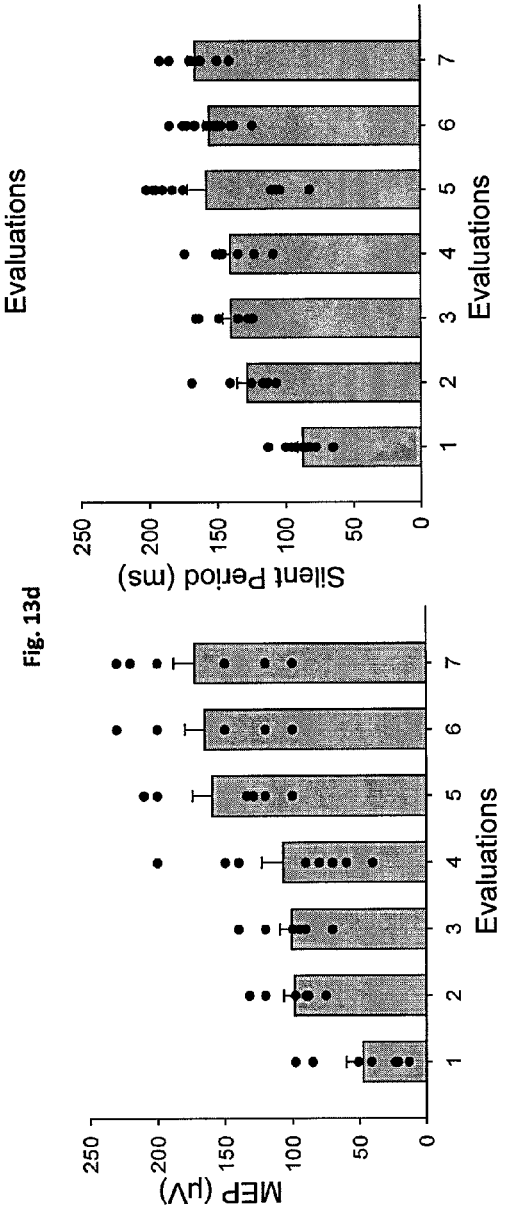
Fig. 13a
Fig. 13b
Fig. 13c
Fig. 13d

Fig. 14a
Fig. 14b
Before
After
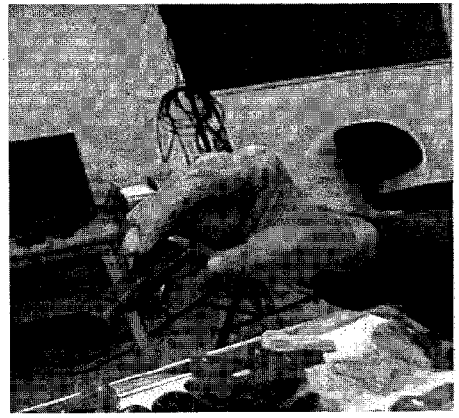

US 9,008,781 B2

METHOD AND SYSTEM FOR TREATMENT OF MOBILITY DYSFUNCTION

CROSS REFERENCE TO RELATED APPLICATIONS

This application is a continuation-in-part of co-pending U.S. patent application Ser. No. 13/503,216, which is a U.S. national stage application under 35 U.S.C. 371 of International Application No. PCT/US10/53720, filed on Oct. 22, 2010, entitled DIPOLE ELECTRICAL STIMULATION EMPLOYING DIRECT CURRENT FOR RECOVERY FROM SPINAL CORD INJURY, which in turn claims priority to and benefit of U.S. Provisional Application No. 61/253,948, filed on Oct. 22, 2009, and U.S. Provisional Application No. 61/316,319, filed on Mar. 22, 2010.

This application is also continuation-in-part of co-pending U.S. patent application Ser. No. 14/157,689, filed on Jan. 17, 2014, entitled CHARGE-ENHANCED NEURAL ELECTRIC STIMULATION SYSTEM, which in turn is a continuation of U.S. patent application Ser. No. 13/635,929, which is a U.S. national stage application under 35 U.S.C. 371 of International Application No. PCT/US11/22283 filed on Jan. 24, 2011, entitled CHARGE-ENHANCED NEURAL ELECTRIC STIMULATION SYSTEM, which in turn claims priority to and benefit of U.S. Provisional Application No, 61/316,319, filed on Mar. 22, 2010.

This application also claims priority to and benefit of co-pending U.S. Provisional Application No. 61/774,207, filed Mar. 7, 2013, and to co-pending U.S. Provisional Application No. 61/780,924.

All of the applications listed above are incorporated herein by reference in their entirety and for all purposes.

BACKGROUND

The present teachings generally relate to the field of providing stimulation of central nervous system tissue, muscles, nerves, or combinations thereof, and more particularly to a system and method for improving neural or neuromuscular communication impairment through multi-point stimulation.

The nervous system comprises the central and the peripheral nervous system. The central nervous system is composed of the brain and the spinal cord, and the peripheral nervous system consists of all of the other neural elements, namely the nerves and ganglia outside of the brain and spinal cord.

Damage to the nervous system may result from a traumatic injury, such as penetrating trauma or blunt trauma, or a disease or disorder including, but not limited to birth defects, cerebral palsy, Alzheimer's disease, multiple sclerosis, Huntington's disease, amyotrophic lateral sclerosis (ALS), diabetic neuropathy, senile dementia, stroke and ischemia.

After spinal cord injury (SCI), spared regions of the central nervous system are spontaneously capable of repairing the damaged pathway, although the process is very limited. Moreover, despite the many promising treatment strategies to improve connections across the damaged spinal cord, the strength of connectivity and functional recovery of the impaired spinal cord are still unsatisfactory.

Electrical stimulation of the central and peripheral nervous systems improves neuronal connectivity, and can be employed to improve functional recovery after neuronal injury. It is an effective method that promotes reactive sprouting through which an increase in the number of functional connections may be possible. Electrical stimulation can also improve functional connections by strengthening the weak existing synapses and/or by promoting synaptogenesis. One of the emerging concepts is that the nervous system contains latent pathways that can be awakened by electrical stimulation or pharmacological manipulation.

The majority of the methods employing electrical stimulation utilize single or dual point paradigm in which unipolar or bipolar stimuli are delivered at points of the challenged neural pathway. The effectiveness of this stimulation depends on active propagation of an action potential.

There is a great desire to improve the effectiveness of electrical stimulation in order to more successfully treat or even reverse neuromotor dysfunctions. Treatment systems can be very complex. There is a need for apparatus that reduces risks while also meeting the need for treatment system that is simpler to operate that still safely improves motor control and function.

BRIEF SUMMARY

Effective systems and methods for improving neural communication impairment of a vertebrate being and affecting motor activity of a peripheral body part are disclosed herein below.

The spinal cord connects with, and communicates the action potential issued by the motor cortex to our distal muscles to drive motor activity. The spinal cord extends along the spine and branches out to the upper and lower extremities to carry such action potential signal to nerve(s) associated with the muscle(s) intended to be actuated. We call this neural transmission path "a neural pathway."

Associative stimulation causes enduring changes in the nervous system based on the Hebbian concept of spike-timing-dependent plasticity. According to the present invention, trans-spinal direct current stimulation (tsDC) modulates associative plasticity. Combining associative stimulation with tsDC has a major and long lasting effect on locomotor recovery in practice of the present invention, in various embodiments thereof, by increasing the amplitude of cortically evoked action potential signal arriving at the target nerve at the dysfunctional muscle.

For purposes of this description, it may be generalized that a neural pathway runs or may be traced from an area of the motor cortex associated with a distal peripheral muscle of interest down the spinal cord and then the pathway branches out to the arm or leg and terminates at the controlling nerve associated with the muscle of interest. The spinal location of this neural branching we refer to herein as a "spinal junction" of the neural pathway. The motor cortex evokes muscle activity by issuing a signal that propagates down the pathway and through the spinal junction down to the target nerve to evoke activity of the muscle of interest.

In several practices of the present invention, triple stimulation of the dysfunctional neuromotor pathway proves to be highly effective in mitigating dysfunction. In an illustrative embodiment, the distal nerve(s) associated with dysfunctional muscle(s) of interest are stimulated with a pulsed stimulation signal (pulsed "distal stimulation"), the spinal junction on the neural pathway of interest is stimulated with a substantially continuous unvarying signal (constant "spinal junction stimulation"), and a location above the spinal junction on that neural pathway through which the cortical action potential passes is stimulated with a pulsed stimulation signal ("pulsed cortical stimulation").

The pulsed cortical stimulation maybe applied for example, by application of electrical or magnetic pulses. The pulsed cortical stimulation is applied at the motor cortex, or along the neural pathway of interest descending from the motor cortex at a location above the spinal junction, about 10 cm above the spinal junction if pulsed magnetic stimulation is used or anywhere above the spinal junction if electrical stimulation is used, provided that if the junction is in lumbar region, then placement is anywhere between thoracic to cervical locations. For cervical location of spinal junction, the pulsed cortical electrical stimulation can be applied at the level of the mastoid processes (bilaterally) to activate the corticospinal tract, (Pulsed magnetic stimulation applied to the cranium is known as trans-cranial magnetic stimulation ("TMS").

The distal and the cortical stimulations each induce responsive signals, i.e., an induced pulsed distal stimulation signal and an induced pulsed cortical stimulation signal which communicate along the neural pathway of interest toward the spinal junction. The spinal junction stimulation signal is applied first to the spinal junction location and then application of the distal and the cortical stimulations are each timed such that their induced signals arrive simultaneously at the already-stimulated spinal junction on that dysfunctional neural pathway According to the present invention, constant spinal junction stimulation, such as tsDC, modulates associative plasticity when combined with associative stimulation, having major and long lasting effect on locomotor recovery. The present invention resolves, reverses, or improves neuromotor dysfunction. Often such dysfunction demonstrates at an underperforming limb, such as a spastic, weak, or paralyzed arm or leg, hand or foot, for example. Large and small nerves can be stimulated. In practice of embodiments of our triple stimulation system, method, and apparatus, the combination of our tsDC paired with associative stimulation, cortical and peripheral, has demonstrated substantial lessening of the dysfunction.

In one or more embodiments, the system of these teachings includes as first signal-providing component configured to provide pulsed peripheral stimulation signals at the peripheral body part of interest, a second signal-providing component configured to provide a pulsed motor cortex stimulation signal to elicit a motor cortex action potential signal, a substantially continuous-level signal-providing component configured to provide DC current, or directional flux stimulation, signal at a neural spinal junction, and a controller component configured to control timing of the pulsed peripheral stimulation signals and the pulsed motor cortex stimulation signal; the timing of the pulsed peripheral stimulation signals and the pulsed motor cortex stimulation signal being controlled such that a peripheral signal from the peripheral body part and a pulsed motor signal from the motor cortex area are substantially simultaneously present at the neural spinal junction when the neural spinal junction is being stimulated by the substantially continuous DC spinal signal.

The latter DC signal is also referred to a cathodal transspinal direct current stimulation, tsDC, and is applied from the cathode of source of level continuous DC stimulation signal, which can include a small ramp at the beginning and end of the signal duration. Other practices of directional stimulation energy sources applied to the spinal junction are also within the scope and practice of the present invention, which by illustration but without limitation of the scope of the invention, in one embodiment could include repetitive TMS, or a cathodal polar stimulation equivalent, if so devised.

In one or more embodiments, the method of these teachings includes providing pulsed peripheral stimulation signals at the peripheral body part, providing a pulsed motor cortex stimulation signal to a motor cortex area, and providing a substantially direct current cathodal spinal stimulation signal at a neural spinal junction, timing of the pulsed peripheral stimulation signals and the pulsed motor cortex stimulation signal being selected such that a backward motor signal from the peripheral body part and a pulsed motor signal from the motor cortex area are substantially simultaneously present at the neural spinal junction when the neural spinal junction is being stimulated by the spinal stimulation signal.

Various other embodiments are disclosed.

For a better understanding of the present teachings, together with other and further needs thereof, reference is made to the accompanying drawings and detailed description and its scope will be pointed out in the appended claims.

BRIEF DESCRIPTION OF THE DRAWINGS

FIG. 4 shows an embodiment of a component of the system of these teachings;

FIG. 5A-D shows an embodiment of the system of these teachings for tsDC+cortico-sciatic and spino-sciatic (CSA) protocols;

FIG. 6A-C shows an embodiment of the system of these teachings for tsDC+spino sciatic (SSA) protocol.

FIG. 11a-f shows before, during and after results for one subject (CP);

FIGS. 12A-B shows three weeks assessments of CP subject of 11a-f;

FIGS. 13A-D show Longitudinal electrophysiological changes recorded from the anterior deltoid muscle in same CP subject of FIGS. 10-12;

FIGS. 14a-b show Right hand grasp during peg-test task before and after treatment (6 weeks) for a Different CP subject.

DETAILED DESCRIPTION OF EMBODIMENT OF THE INVENTION

Figure 1:
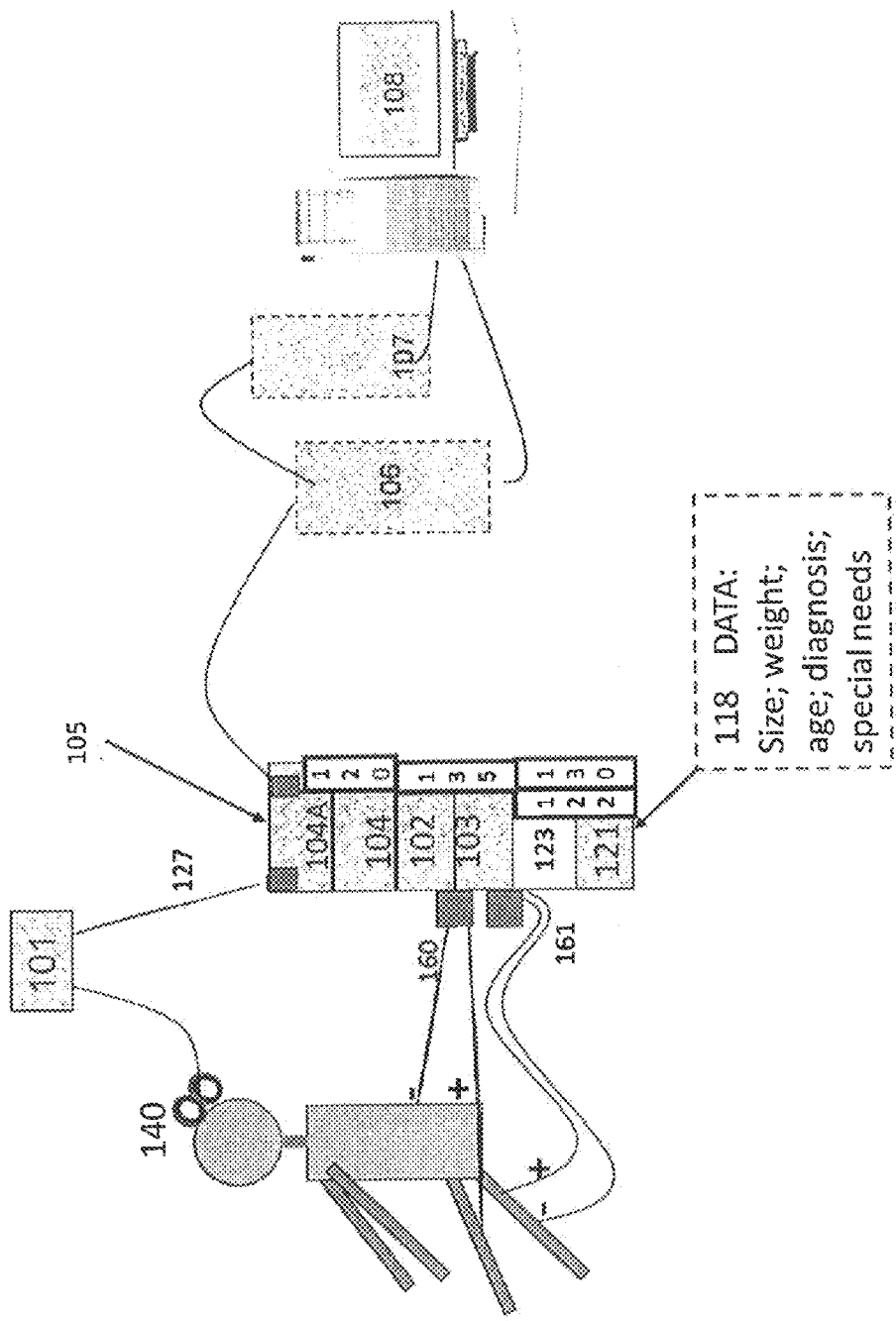
FIG. 1 shows one embodiment of the system of these teachings.

The following detailed description presents the currently contemplated modes of carrying out the invention. The description is not to be taken in a limiting sense, but is made merely for the purpose of illustrating the general principles of the invention, since the scope of the invention is best defined by the appended claims.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about."

Effective systems and methods for improving neural communication impairment of a vertebrate being and affecting motor activity of a peripheral body part are disclosed herein below.

One embodiment of the present teachings, method and apparatus, provides a system and method for paralysis treatment that addresses mobility dysfunction by improving motor signal transmission from motor cortex to distal muscles. Substantial reversal of paralysis and of related dysfunction has been demonstrated in laboratory mice and in human subjects. In various embodiments the mobility treatment of the present teachings is administered through operation of the disclosed stimulation treatment center.

One embodiment of the present mobility treatment is applied to suspect motor pathway to reverse the neuromotor signal transmission disorder that apparently is retarding muscle function. Dysfunction is treated regardless of the original cause of such dysfunction. The treatment has demonstrated reversal of paralysis or of other degraded mobility conditions upon a variety of pathologies.

The treatment is based upon a combination of timed cortical, spinal cord and associated nerve/muscle stimulations. In one instance, three simultaneous stimulation signals are applied at strategic locations along a diagnosed failing neural motor pathway to improve transmitted motor signal to the distal muscle. In an illustrative treatment, constant level trans-spinal direct current (tsDC) stimulation is applied to the surface area above the spinal neural junction where the subject neural pathway branches out to the target muscle(s). Sponge electrodes or contact gel are used to assure delivery of a continuous constant level trans-spinal DC stimulation at the spinal junction as well as managing current density of the applied stimulation.

In an illustrative practice of the invention includes a combination of stimulations, including pulsed stimulation of an area of the motor cortex which is associated with the dysfunctional target muscle and pulsed stimulation applied to the nerve area associated with the dysfunctional target muscle. The motor cortex stimulation is non-contact pulsed magnetic stimulation, or alternatively stimulated with pulsed DC electrical stimulation. The peripheral nerve is stimulated with pulsed DC. The electrical stimulations are achieved with conventional electrodes.

In an illustrative embodiment, stimulation of motor cortex and distal muscles is generally known as paired associative stimulation (PAS). We use a modified form of PAS, by applying two pulses in one cycle to create dual peripheral pulses to induce changes at the cortex (long delay pulse) and at the spinal cord (short delay pulse) during the triple stimulation protocol. The effect of the unique combination of simultaneous tsDC and any PAS is to substantially enhance motor signal transmission within the failing pathway. Now an enhanced motor signal is applied to the muscle of interest, with the result of measured improvement in mobility (measurable in strength, speed, range of motion, and/or dexterity, etc.).

In one or more embodiments, the system of these teachings includes a first signal-providing component configured to provide pulsed peripheral stimulation signals at the peripheral body part, a second signal-providing component configured to provide a pulsed motor cortex stimulation signal to a motor cortex area, a substantially constant current DC signal-providing component configured to provide relatively constant level direct current spinal stimulation signal at a neural spinal junction and a controller component configured to control timing of the pulsed peripheral stimulation signals and the pulsed motor cortex stimulation signal. In one practice, several peripheral pulses occur per cortical pulse. The timing of the pulsed peripheral stimulation signals and of the pulsed motor cortex stimulation signal is controlled by the controller such that a backward motor signal from the peripheral body part and a descending motor signal from the motor cortex are substantially simultaneously present at the neural spinal junction when the neural spinal junction has been and is being stimulated by the substantially constant DC signal.

In one configuration, the substantially DC signal-providing component active electrode provides cathodal stimulation at the spinal junction. In a further instance, the controller component is configured to provide the direct current spinal stimulation signal at the neural spinal junction before the pulsed peripheral stimulation signals and the pulsed motor cortex stimulation signal are applied, and subsequently to provide a first pulse as a peripheral stimulation signal to the nerve at the muscle of interest, and provide, after a time delay after providing the first pulse, a second pulse of the peripheral stimulation signal to the nerve at the muscle, and provide, after another time delay after providing the first and second pulses, the pulsed motor cortex stimulation signal, the time delay and the other time delay being selected such that a backward motor signal from the stimulated nerve for the muscle and the pulsed motor signal from the motor cortex are substantially simultaneously present at the neural spinal junction when the neural spinal junction is being stimulated by the substantially DC signal.

In the embodiment of FIG. 1 peripheral stimulator 103 issues pulsed DC stimulation to the patient via the +/− leads, shown extending from i/o connector 161. The leads are affixed at the nerve associated with the dysfunctioning muscle. Peripheral stimulation electrodes are positioned on the nerve and can be placed at the main nerve trunk to stimulate a large group of muscles. Placement is at the nerve associated with muscle or muscles with dysfunction. For example, the electrodes could be placed on leg, behind knee, on the foot, on arm, at wrist or shoulder, all depending upon the target for that patient.

Various Embodiments

An embodiment of the system of these teachings is shown in FIGS. 1-4, wherein stimulation system 100 includes a first stimulator 101 that provides motor cortex stimulation. In one exemplary embodiment, the first simulator 101 could be, for example, but not limited to, a conventional pulsed magnetic stimulator or a conventional pulsed DC stimulator. A second stimulator 102 provides continuous trans-spinal DC stimulation 160 to the neural spinal junction. In an exemplary embodiment, the second stimulator could be, but is not limited to, a conventional source of continuous DC stimulation capable of delivering a continuous selected low current signal, with minimal variation, and using sponge electrodes and with a short ramp-up and ramp-down at the beginning and end of stimulation, all to mitigate startup and shut down artifacts. A third stimulator 103 provides stimulation of the peripheral nerve(s) associated with a dysfunctional area/muscle(s) of interest, in an exemplary embodiment, the third stimulator can be, but is not limited to, a conventional pulsed stimulator capable of delivering pulsed DC stimulation.

Stimulator 101 provides pulsed stimulation to the motor cortex. For example, this may be pulsed magnetic or DC electrical stimulation, and may be a stand-alone unit or incorporated within control center 105. In an illustrative embodiment of system 100, magnetic stimulator 101 is included as a standalone magnetic stimulation system for non-contact delivery of pulsed magnetic stimulation to the motor cortex.

Control center 105 further includes system controller/synchronizer 104 configured to control and/or synchronize the stimulators 101, 102, 103, and in one embodiment includes a non transitory computer usable medium (such as, but not limited to, RAM) 123 and an I/O component 104A to provide synchronization, control and or timing signals from controller 104 to external stimulators, such as to the first simulator 101. In the illustrative embodiment of FIG. 1, controller/synchronizer 104 at I/O 104A delivers a trigger signal 127 to trigger stimulator 101 according to practices of the invention further discussed below.

In an illustrative embodiment, the system further includes support equipment including channel amplifier 106, data recorder 107 (which may also include capture of muscle motor evoked potential and EMG), and computer 108, where the computer further supports synchronization, control and/or stimulation and data acquisition. Computer 108 and or the system controller/synchronizer 104 can, in one embodiment, include one or more processors 120 and computer usable media 130, as further shown in FIG. 4, where the computer usable media has computer readable code embodied therein that, when executed in the one or more processors, causes the one of more processors to perform the method of these teachings. In the embodiment shown in FIG. 4, the one or more processors 120 are operatively connected to the computer usable media 130 by means of a connection component, such as a computer bus 135.

Figure 2A:
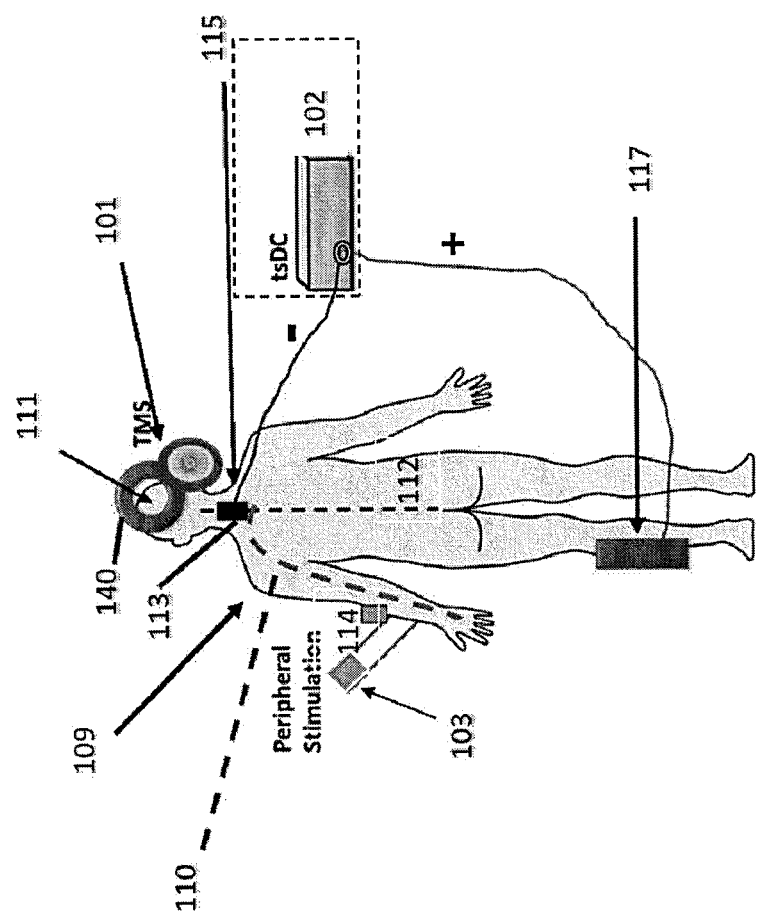
FIGS. 2a, 2b show an application of one embodiment of the system and method of these teachings.

FIG. 2a shows a further embodiment of the invention, including trans-spinal stimulator 102, a sponge electrode 115 providing cathodal stimulation placed upon the appropriate spinal column segment. In practice of embodiments of the invention, for upper extremity stimulation, sponge electrode 115 is placed at cervical segment in the area of C6 to T1, and for lower extremity is placed in the area of T10 and L1 vertebral levels. These areas have known associations with distal nerves related to target muscles of interest, as will be appreciated by those skilled in the art. The return electrode is placed at a bony location such as at the lower leg.

In an illustrative embodiment, during treatment, patients are seated comfortably in armchair. The cathodal tsDC electrode 115 is applied over the appropriate spinal column segment, e.g., segment 113. TMS coil is placed over the motor cortex representation of upper extremity for upper extremity group or over the representation of the lower extremity for lower extremity groups. The peripheral electrodes are placed over the nerve of interest.

In an illustrative practice, tsDC and TMS stimulations are be applied at the commencement of the session and remain on for the duration, simultaneously with multi-pulse peripheral stimulation. The conventional 10/20 system is used to locate the appropriate placement of the coil (or alternatively electrode) stimulation at the cortex, as will be understood by a person skilled in the art. Typical stimulation sessions run for 20 minutes and are repeated as needed, several times per week, over a number of weeks, and as per level of improvement of the treated muscle(s) of interest.

An evoked potential or evoked response is an electrical potential of the nervous system generated following presentation of a stimulus, as distinct from spontaneous potentials as detected by electroencephalography (EEG), electromyography (EMG), or other electrophysiological recording method. In a practice of the invention, during stimulation, motor evoked potential (MEP) is recorded conventionally via bipolar surface electrodes of fixed inter-electrode distance of 2.5 cm and EMG is recorded from ipsilateral and contralateral (in relation to stimulated motor cortex) muscles in the upper and lower extremities as needed.

In an illustrative embodiment, stimulation intensity is adjusted to about 115% of the active threshold. Active motor threshold is defined as the minimum stimulus intensity that produces a consistent motor evoked response. In an illustrative embodiment, magnetic stimulation of stimulator 101 is applied at a frequency of 0.3 Hz. In an illustrative "figure-eight" magnetic stimulator coil 140 is used to apply such stimulation, shown in FIG. 2a and in FIG. 3, the latter as part of an illustrative system 100 operating in conjunction with a patient platform, such as a medical chair 142, both of which would provide for the comfort of the patient during sessions. In one exemplary embodiment, motor cortex stimulation is carried out using coil 140 positioned over the M1 region, shown in FIGS. 2a and 3. In other exemplary embodiments, motor cortex electrical stimulation is carried out using one or more electrodes for effecting motor cortex stimulation.

In an illustrative, but not limiting embodiment, TMS is done with Figure-of-eight coil 140 positioned over the M1 region (as such region is known to those skilled in the art). Subjects are seated comfortably in an armchair. The head is strapped to a head-rest to prevent movement relative to coil 140. The coil is placed tangential to the skull. The coil is held stably by a coil stand or the like that allows easy adjustment.

In an illustrative embodiment, stimulator 102 delivers trans-spinal direct current stimulation (tsDC) to the spinal junction of interest 113 and is held at a safe constant current, ranging up to about 5 mA, or higher, depending upon patient tolerance of felt effect. Typical session is twenty minutes. The active cathodal electrode of stimulator 102 (stimulator 102 "−") is placed over the selected upper or lower area of spinal segment of the spinal column. As shown in the non-limiting illustration of FIG. 2a, for treatment of an upper extremity motor dysfunction issue, sponge electrode 115 is applied to the upper spine around C6 to T1 and the return sponge electrode 117 is placed over a non-critical, non-nerve, location such as the bony part of the leg, as shown. Sponge electrodes are used to deliver the constant level trans-spinal DC stimulation at the spinal junction without uncomfortable artifacts. A large sponge electrode 117 is used on the positive return electrode at the leg.

As will be appreciated by those skilled in the art, the size of the active cathodal sponge electrode 115, i.e., the amount of surface area presented to the skin at the spine, is selected according to safety considerations in view of the level of energy being applied, current density, energy dissipation considerations, and known characteristic data of the patient. Illustrative, non-limiting examples of such patient characteristics may include size, weight, age, diagnosis, prior medical history, and special needs, for example. In an illustrative embodiment, such data 118 is loaded into system 100 at control center 105.

Embodiments of the present invention are derived from simultaneous conditioning of the spinal neurons at the spinal junction of interest by applying constant trans-spinal DC stimulation at the spinal junction combined with repetitive stimulation to affect the cortex, applied to the motor cortex or an extension thereof or proxy therefor, for evoking cortical pulses, and pairs of pulsed peripheral stimulation applied to the distal nerve at the target limb and muscle(s) of interest for evoking multiple peripheral evoked pulses one for cortical stimulation and one for spinal stimulation. The peripheral stimulation of the target limb is synchronized with motor cortex stimulation during continuous application of trans-spinal stimulation at the spinal junction.

Generally, the distal electrodes are placed on or about a nerve of the upper extremity for upper extremity treatment and of the lower extremity for the lower extremity treatment.

The electrodes are placed across the nerve area so as to pass current therethrough. In an illustrative embodiment, a pulsed DC stimulation is applied to the limb muscles (leg, arm, etc.). Conventional stimulation electrodes are positioned at limb nerve(s) of interest. In a large target, one electrode may be placed close to the main nerve trunk to stimulate a large group of muscles and the other electrode is offset on such neural area to define the distal neural stimulation path.

Exemplary and illustrative embodiments of simulators, stimulation, electrodes and magnetic field producing components are disclosed herein. It should be noted that these teachings are not limited to only these embodiments and that these embodiments are presented to further elucidate these teachings without limitation of the breadth and scope of the disclosed invention.

In practice of embodiments of the invention, the desired position of coil 140 is defined as the location where TMS stimulation evokes the strongest contralateral extremity MEP. Surface electromyography (EMG) can be recorded from the muscles by use of adhesive electrodes in a belly montage. Motor cortex excitability is measured by determining the resting and active motor thresholds of muscles of the upper extremity, such as anterior deltoid, biceps brachii, triceps brachii, flexor carpi ulnaris, extensor digitorum, and abductor pollicis brevis. Assessing changes in this group of muscles gives understanding of functional changes in the whole upper extremity following the treatment, as will be understood by a person skilled in the art.

In an illustrative, but non-limiting embodiment, threshold is defined as the intensity of stimulation required to elicit a detectable MEP during either rest or muscle contraction. Rest is determined by monitoring EMG not to exceed a low level blow 0.5 mV, and not to exceed 0.01 mV. Active threshold is measured for each muscle of interest while the subject maintains contraction against gravity. For example, subjects would maintain the wrist joint in near full range when testing the wrist extensor threshold, in this illustration.

The transcranial stimulation is performed in this embodiment using a MagStim Rapid2 stimulator. Muscle motor evoked potential is recorded via bipolar surface electrodes of fixed inter-electrode distance of 2.5 cm. EMG is recorded from ipsilateral and contralateral (in relation to stimulated motor cortex) muscles in the upper or lower extremities. The intensity is adjusted to 115% of the active threshold. This is also equal to 95% of resting motor threshold. Active motor threshold is defined as the minimum stimulus intensity that produces a consistent motor evoked response.

In an illustrative embodiment, pulsed stimulation of the motor cortex in an adult ranges at 100-400 mA, around 200, pulse width of 100-300 microseconds, around 200, 0.5 to 3 Hz repetition rate, operating voltage 400-800. For a child, 70-100 milliamps at 100 microseconds is a target. Magnetic stimulation is applied similarly, as will be understood by a person skilled in the art. In an illustrative pulsed magnetic stimulation is delivered at a rate of 0.5 to 3 Hz, 200 microsecond pulse width, reaching stimulation current levels equivalent to electrical stimulation.

To calibrate the peripheral stimulation, we increase the pulsed DC to as high level that the patient can tolerate, adjusting the current intensity until the whole target muscle group/s is twitching, although this is adjusted based on patient tolerance. The two criteria are to adjust the peripheral pulse intensity for patient tolerance and muscle contraction. The more contraction the higher the enhancement. There must be a balance between the patient tolerance of pain and the amount of muscle contraction to produce desired results. These tolerance levels are session specific and must be detected at each session.

In practices of the present invention a magnetic stimulator coil that produces a flux density of 1.5 tesla has been used. Stimulation at about 75-85% of the maximum has been successful at a frequency of 0.3 Hz, i.e., one pulse every 3 seconds, continuous for the session. A non-limiting maximum stimulation level is set at 1.5 tesla for average normal stimulations.

In one embodiment, peripheral stimulation is provided with a Digitimer Stimulator (model DS7AH) to stimulate peripheral muscles. Stimulation electrodes are positioned close to the main nerve trunks to stimulate a large group of muscles, or close to a single nerve to more narrowly focus this treatment to one target muscle. The electrodes are placed on upper extremity for upper extremity protocol and lower extremity for the lower extremity protocol.

In one or more embodiments, the method of these teachings includes providing pulsed peripheral stimulation signals at the peripheral body part, providing a pulsed motor cortex stimulation signal to a motor cortex area, and providing a constant direct current spinal stimulation signal at a neural spinal junction, timing of the pulsed peripheral stimulation signals and the pulsed motor cortex stimulation signal being selected such that a backward motor signal from the stimulated peripheral body part and a pulsed motor signal from the motor cortex area are substantially simultaneously present at the neural spinal junction when the neural spinal junction is being stimulated by the constant direct current spinal stimulation signal.

Figure 2B:
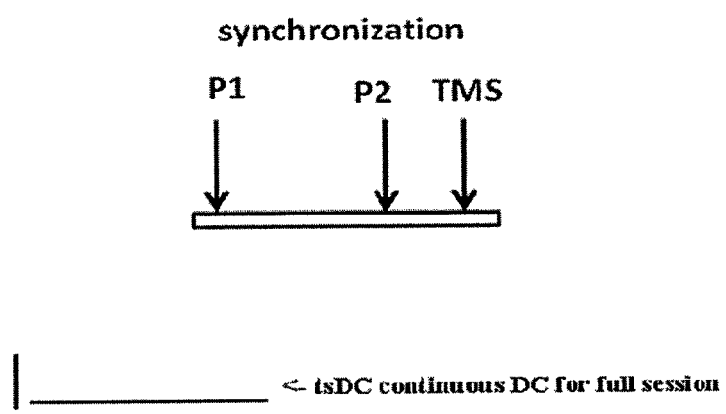
Figure 3:
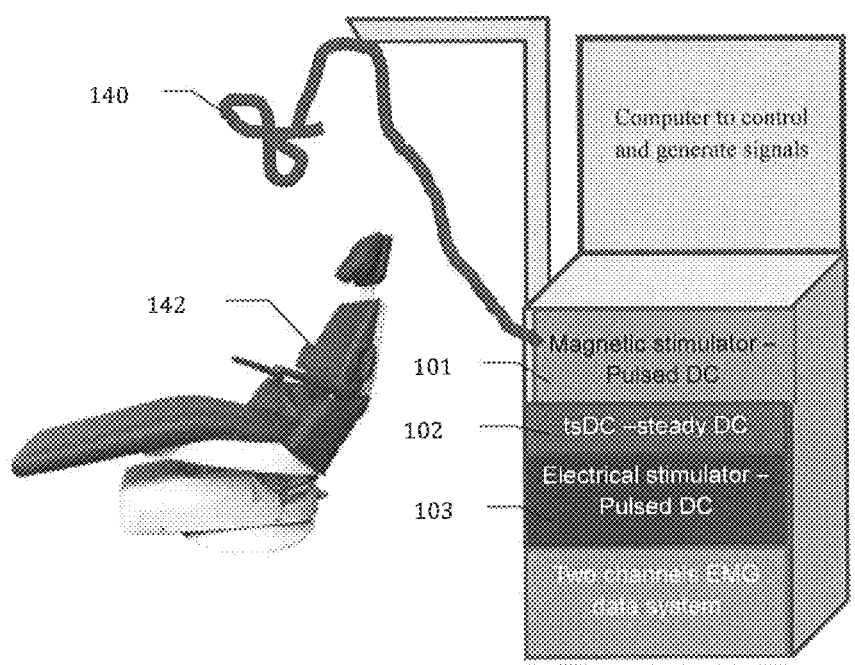
FIG. 3 shows another embodiment of the system of these teachings.
Figure 7A:
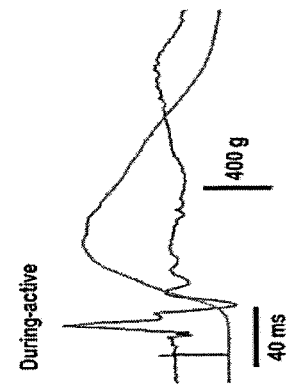
FIGS. 7A-D shows the results of one exemplary application of the method and system of these teachings.
Figure 7B:
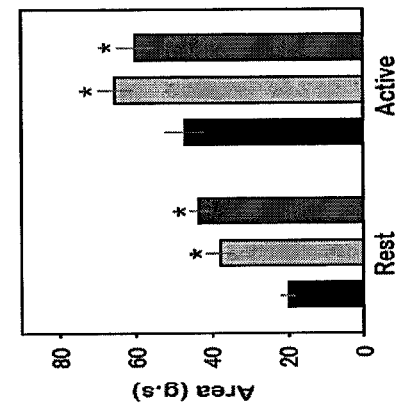
Figure 7D:
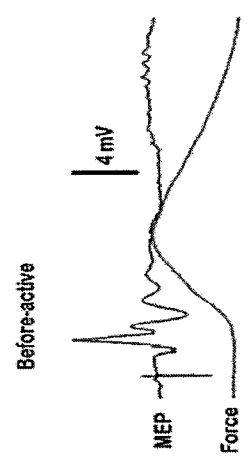
Figure 7C:
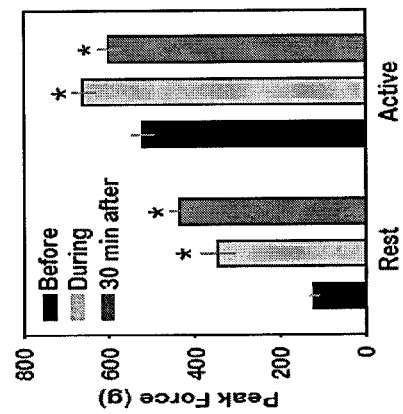

Referring to FIG. 2a in conjunction with FIG. 2b, an application of one embodiment of the system and method of these teachings is shown, wherein a neural pathway 110 is identified by dotted line running from motor cortex 111 down the spinal cord 112 to the location of a neural spinal junction 113 whereupon the neural pathway 110 branches out from the spinal cord and extends down to the peripheral upper limbs, i.e., to arm 109 and the distal nerves/muscles 114 of interest. Neural pathway 110 connects the motor cortex 111 to the distal nerves/muscles 114 by way of the spinal junction 113. The present stimulation invention increases the motor cortex action potential arriving at the distal nerves/muscles 114 by stimulating spinal neuromotor excitability resulting in amplified motor activity and improved function and mobility.

In an illustrative practice of the invention, direct current spinal stimulation signal is provided at the neural spinal junction 113 to begin the protocol, and then the pulsed peripheral stimulation signals and the pulsed motor cortex stimulation signal are applied. More specifically, after spinal stimulation is applied, system controller/synchronizer 104A applies a first stimulation signal to stimulator 103 to apply a first stimulation pulse to the peripheral nerve associated with an underperforming muscle of interest in a distal area. After a first time delay after providing the first pulse P1, a second pulse P2 is provided as the next peripheral stimulation signal to the nerve serving the muscle of interest in the distal area. After a second time delay following from providing the second pulse, the pulsed motor cortex stimulation signal is applied. The first and second time delays are selected such that a so-called "backward"-going motor signal on the neural pathway from the nerve/muscle in the distal area flows toward the neural spinal junction while the pulsed motor signal from the motor cortex flows to the neural junction, all on the neural pathway of interest, and as a result they are substantially simultaneously present at the spinal junction when the neural spinal junction is being stimulated by the continuous trans-spinal direct current stimulation signal. The time delays are adjusted for delay in signal travel from start to end, e.g., from start of peripheral signal assent toward spinal junction to arrival at spinal junction. The actual time delay depends upon the distance to be traveled and is adjusted accordingly, further discussed below.

The pulsed motor cortex stimulation may be electrical or otherwise. In an illustrative instance, the pulsed motor cortex stimulation is provided by pulsed magnetic field signal generated by TMS. At times, the pulsed motor cortex stimulation is referred to hereinafter for convenience, and not as a limitation, as TMS. It will be understood that such TMS stimulation may be provided by non-TMS pulsed stimulation within the practice of embodiments of the invention.

In an illustrative embodiment, the direct current spinal stimulation signal, provided as trans-spinal direct current stimulation (tsDC), is applied first and remains at a continuous and fixed level of DC current (i.e., not substantially varying) while the other stimulation signals are being applied simultaneously the target spinal junction of interest. A first pulse P1 is provided as a first peripheral stimulation to the nerve associated with the target needy muscle in a distal area. A first time delay after P1, a second pulse P2 is provided as a second peripheral stimulation signal to that nerve. After a second time delay after providing the second peripheral stimulation signal, the pulsed motor cortex stimulation signal (e.g., TMS) is provided to the motor cortex area. The first time delay and the second time delay are selected such that a motor signal traveling from the nerve at the target distal muscle to the spinal junction and the pulsed motor signal from the motor cortex to the spinal junction are substantially simultaneously present at the spinal junction when the spinal junction is simultaneously being stimulated by the direct current spinal stimulation signal. The motor signal traveling from the nerve at the target distal muscle to the spinal junction may be said to be reflecting or traveling backward, in the sense that the normal neural signal flow is from the spinal junction to the nerve of interest.

It will therefore be understood that, in an illustrative embodiment, the distal nerve is doubly stimulated, with a first evoked response of the nerve providing a first stimulation signal that will travel to the brain and activate the somatosensory cortex to enhance effect of the next direct cortical stimulation from the controller/synchronizer 104, and then a timing signal is applied by controller/synchronizer 104 to evoke the next direct stimulation of the motor cortex to generate a pulse stimulation signal destined for the spinal junction, and controller/synchronizer 104 applied a timing signal to the distal nerve to evoke a pulsed signal which will travel on the neural pathway backward toward the spinal junction, both timed to impact the spinal junction simultaneously with the tsDC stimulation at the spinal junction.

In a further embodiment demonstrating motor improvement, such as after spinal cord injury, in practice of embodiments of the invention cathodal tsDC is combined within a cortico-sciatic associative (CSA) stimulation protocol, i.e., during tsDC there is a evoked pulsed stimulus from a distal nerve related to a neuromuscular dysfunction and another evoked pulsed stimulus from the motor cortex, both of which traverse the connecting neural pathway and are present simultaneous during tsDC stimulation at the spinal junction, in practice of the invention. In an illustrative embodiment, the nerve is doubly stimulated, with first evoked response of the nerve providing a first stimulation signal and then a timing signal is applied by controller/synchronizer 104 to evoke the next direct stimulation of the motor cortex to generate a pulse stimulation signal destined for the spinal junction, and a timing signal is applied to the distal nerve to evoke a pulsed signal which will travel on the neural pathway backward toward the spinal junction, both timed to impact the spinal junction simultaneously with the tsDC stimulation at the spinal junction.

In another embodiment, demonstrating motor improvement, such as after spinal cord injury, in practice of embodiments of the invention, cathodal tsDC is combined with a spino-sciatic associative (SSA) stimulation protocol, i.e., during tsDC there is evoked a pulsed stimulus at the target distal nerve and a pulsed cortical stimulus evoked at a spinal cord location as local proxy for direct stimulation at the motor cortex. Otherwise, the protocol proceeds similar to the CSA, but the cortical stimulation is achieve without direct stimulation on the motor cortex.

Applying SSA or CSA with tsDC stimulation markedly enhances their immediate and long-term effects as opposed to SSA or CSA only. In each protocol, stimulation produces immediate enhancement of the induced spinal and cortical outputs, respectively, depending on the duration of the interstimulus interval, in which repetitive SSA or CSA stimulation produces long-term potentiation of spinal and cortical outputs, respectively. Applying SSA or CSA during tsDC stimulation markedly enhances their immediate and long-term effects.

In one embodiment, behaving mice with unilateral SCI, four consecutive 20 min sessions of CSA plus tsDC markedly reduced error rate in a horizontal ladder-walking test. This form of artificially enhanced associative connection translates into a form of motor relearning that does not depend on practice or experience. Remarkably, favorable results were seen near-term. In another embodiment, repetitive SSA plus tsDC induced a significant improvement compared with baseline data during application and a significant increase of posttest performance compared with pretest.

For direct electrostimulation of the motor cortex, the cathode is placed at the motor cortex location and then the reference electrode is placed nearby. EEG electrodes can be used for the cortical stimulation along with conductive gel.

For SSA stimulation, an extension, or proxy, of the motor cortex is used. In an illustrative embodiment, for upper limb treatment, the electrodes are placed on the mastoid location on the head. In another illustrative embodiment, for lower extremity, the thoracic spine can be used. In either case the spinal junction lies in between the cortical and peripheral stimulation sites on the pathway of interest.

As shown in FIGS. 5-6, additional uses are also within the practice of the present invention, wherein the triple stimulation was successfully combined with either SSA or CSA in treatment of subjects. Reference is made to the text of that FIGS. 5-6.

Further exemplary embodiments are disclosed herein below. These teachings are not limited only to the exemplary embodiment and that the exemplary embodiment is provided to elucidate these teachings.

In an illustrative embodiment of the synchronization timing protocol illustrated in FIG. 2b, a stimulation cycle is initiated with a first distal stimulation pulse (P1) being applied by stimulator 103 to a peripheral nerve serving the distal muscle of interest. After some time delay, a motor cortex pulse (TMS) is applied to the motor cortex by stimulator 101. Prior to applying that TMS pulse, a second pulse (P2) is applied to the same peripheral nerve by stimulator 103. The P2 pulse at the nerve is applied earlier because the peripheral nerve signal that is generated will take longer to arrive at the spinal junction than the TMS-generated cortical pulse will take to arrive there. The tsDC is applied to the area of the spinal junction continuously for the session.

The first pulse applied to the peripheral nerve initiates a sensory response at the site of stimulation. This sensory response will travel to the brain and activate the somatosensory cortex having an effect during the time when the cortical pulse will be applied to the motor cortex. In embodiments of the invention, the timing is thus set to achieve the desired simultaneous triple stimulation of the spinal junction as part of this invention.

In one illustrative embodiment, treating a dysfunction muscle of the arm, the two peripheral pulses are applied before the cortical pulse. One peripheral pulse is delivered at approximately 30 ms before the cortical pulse and a second peripheral pulse is delivered with a delay ranging between 3 to 1.2 ms before the TMS pulse. Now the motor cortex-issued pulse will arrive at the neural junction in approximately 4-6 ms to meet the peripheral pulse from the arm. One impact of this paradigm is to strengthen the connection between the primary motor cortex and the spinal cord.

TABLE 1

Peripheral delay: Estimating the inter-stimulus intervals (ISI):

| Stimulated site | F-wave delay (average) | Final estimated peripheral delay |
|---|---|---|
| Wrist (median or ulnar nerve) | F-wave = 23-25 | (11-13 ms) |
| Elbow (median or ulnar nerve) | F-wave = 15-16 | (7.5-8 ms) |
| Ankle (peroneal nerve) | F-wave = 45 | (22.5 ms) |
| Knee (peroneal nerve) | F-wave = 27 | (13.5 ms) |
| Ankle (tibial nerve) | F-wave = 44 | (22 ms) |
| Knee (tibial nerve) | F-wave = 27.6 | (14 ms) |

Illustrative embodiment of estimation of peripheral delay (the time of the antidromic action potential) from the site of stimulation to reach the motoneurons' cell bodies residing in the spinal cord, reliance is placed on known F-wave literature, F-wave represents the time of the following processes: 1) action potential generation at the site of stimulation; 2) action potential backward propagation (toward the spinal cord or antidromic); 3) the time of initiation at the initial segment at the origin of the axon; 4) the time of forward propagation (orthodromic) to the peripheral site. Out of all these processes, the two with the significant delay are the antidromic and the orthodromic. After considering all these processes, the final estimated peripheral delays are shown in table 1.

Estimating the central delay (corticospinal pathway): This was obtained from known literature in which spinal potential was directly recorded from the surface of the spinal cord in response to cortical motor stimulation. From these reports, the delay of the Corticospinal Volley recorded at the cervical region is 4.17 ms with electrical stimulation and 4.0 with TMS. The delay of corticospinal volleys recorded from the lumbar cord extend from 8 to 14 ms.

The above data—peripheral and corticospinal delays—used to estimate the ISI that should be used to make the associative event to occur at the level of the spinal cord. As seen in the above data, the peripheral delay is always longer than the central one. Therefore, the peripheral electrical pulse would always start before the cortical pulse, and the ISI would equal peripheral delay minus corticospinal delay.

In review of motor evoked potential (MEP) for each subject, the total delay (peripheral plus corticospinal) will equal the MEP delay for that subject. A chart of the initial ISI for different body location is shown in Table 1. This ISI is programmed in the computer used to generate the stimulating protocol.

Pulsed DC or magnetic stimulation has been used on the cortex. DC can be applied directly to the brain, without negative effect, but magnetic stimulation is beneficial because there is no artifact at the skin surface. Pulsed DC is used for peripheral stimulation. In one embodiment of the method of these teachings, the method includes the spinal tsDC, and with motor cortex and distal peripheral stimulation (augmented with electric-induced somatosensory stimulation from the distal muscle to the motor cortex), to treat subjects with stroke, cerebral palsy, and the like, as well as healthy subjects, for improved motor function.

In order to further elucidate these teachings, results from an exemplary human study embodiment are presented below, wherein eleven (11) subjects (N=11) were treated as part of a CP/Stroke ("CP/S") study. CP/S study consists of six healthy subjects who were treated for two sessions (one sham and one real) over two weeks, plus four CP patients and one stroke patient treated over six weeks.

Analyzed data from CP/S study is consistent with the preclinical data gathered from our animal studies demonstrating that behavioral recovery can be induced by the combined and timed cortical, spinal cord and associated muscle stimulations of the Present protocol and that this type of artificially-induced associative connection translates into a form of motor learning that does not depend on practice or experience.

The most obvious mechanism of action by which behavioral improvements have occurred with the present treatment is based on direct strengthening of the neuromotor pathway by tsDC plus PAS applied to spared or newly sprouted descending motor connections contralateral to the injury. This stands as a positive expression of neuroplasticity and transference, where plasticity in one circuit promotes concurrent or subsequent plasticity in another.

A practice of the invention is discussed in the publication, J. Neurosci. 2013 Mar. 13; 33(11):4935-46, which is incorporated herein by reference in its entirety for all purposes, and is part of referenced provisional application.

Further Treatments in Humans

I. Normal Subjects: N=6

Electrophysiological assessment:

Six normals ("healthy") participated in two sessions (one per week). One session was a sham. In the active session of Present protocol, the six normal subjects were treated and demonstrated cortically evoked muscle contractions and amplified potentials, see composite graph of FIG. 7a-d. The sham treated-subjects showed no amplification. In the sham experiments subjects were prepared in the same way as in the real treatment except that tsDC+(−) was quickly turned on and off. (Sham not shown.)

Figure 8:
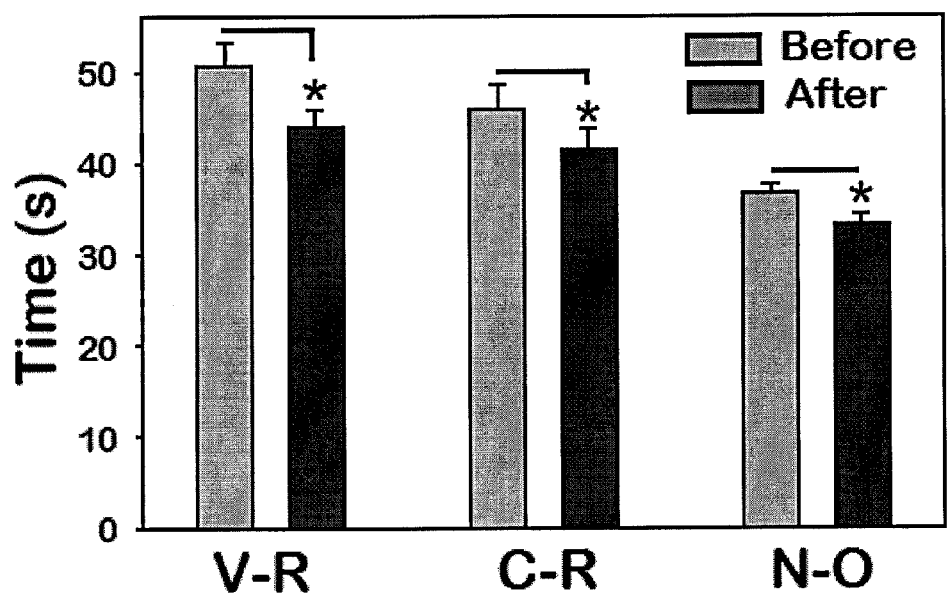
FIG. 8 shows peg test where treatment for hand yields shortened peg-board time in normal subjects.

Review of results of dexterity tests before and after Present protocol demonstrates a shortening of time in both peg-test and eight-position test. FIG. 8 shows shortened peg-board time done under three levels of difficulty after the treatment. The peg test levels of difficulty; variable-reverse (V-R), constant-reverse (C-R), and no-order (N-0). Additionally, muscle strength (grip and pinch) was increased (not shown).

Figure 9:
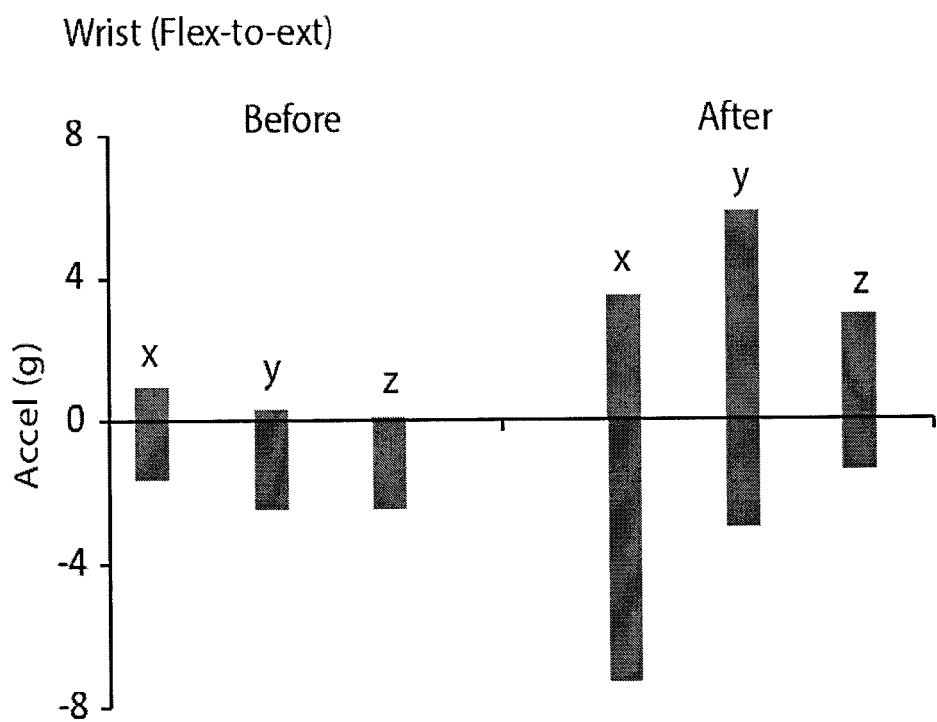
FIG. 9 shows acceleration of the movement at the wrist joint increased significantly after full treatment.

FIG. 9 shows acceleration of the movement at the wrist joint increased significantly after full treatment. Longer bars after treatment show greater acceleration and better grip function. As shown in FIG. 9, the speed of joint movements (acceleration) was significantly improved following the one session of the Present protocol. Acceleration of movement at the wrist joint increased significantly after the treatment. Longer bars after treatment show greater acceleration as a measure of improved motor control and function.

II. Subjects with Cerebral Palsy: N=4

Although all 4 patients showed significant improvements in functional recovery, analyzed results are currently available for one of the CP subjects as shown below in FIGS. 10-12 and before/after pictures are available for another CP subject (FIG. 13).

Figure 10:
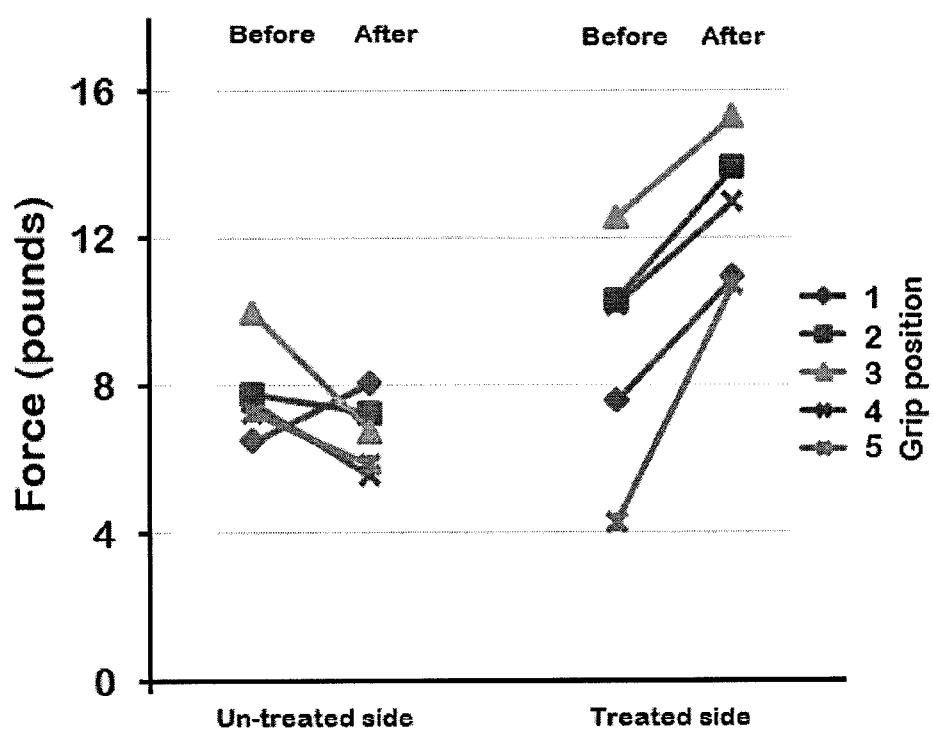
FIG. 10 shows three weeks assessment of strength improvement of one subject with cerebral palsy: Untreated side was unchanged. Treated side evidences significantly improved strength of handgrip capability.

FIG. 10 shows three weeks assessment of one subject with cerebral palsy. On the treated side (right side), the combined treatment has significantly improved the strength of the handgrip capability, while the handgrip ability on the untreated side was not changed. Using a hand grip tool, the force at five gripping positions was measured. Force is in pounds. Improvement is major and enabling.

In FIG. 11, the same subject from FIG. 10 was unable to lift right arm or to articulate thumb before treatment (before). After three weeks, subject could partially lift arm but with limited rotation at shoulder; thumb not articulated (3 weeks). After six weeks of treatment, subject was able to raise and hold arm high and to usefully articulate thumb (after).

Figure 12A:
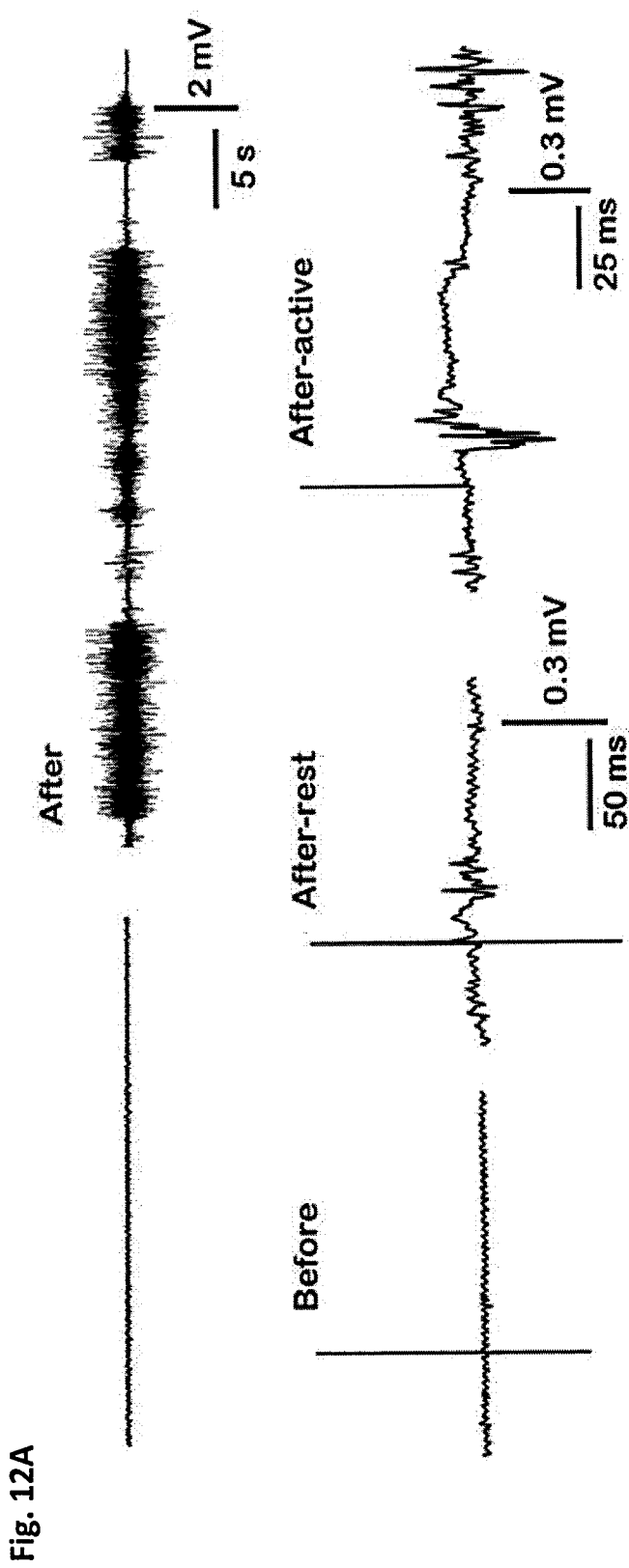

FIG. 12 shows three week assessment of same CP subject of FIGS. 10-11. In A, the EMG brain trace shows the voluntary contractions of the treated abductor polici brevis muscle of the right hand (treated side). Before the treatment the participant was not able to contract the right thumb into abduction (outward movement) as indicated by no EMG activity (A, before). However, after three weeks of treatment the patient was able to generate movement as shown by the increase in EMG activity (A, after).

As shown in B, the motor evoked potential recorded from the abductor polici brevis muscle was significantly improved. MEP was minimal before the treatment (before). Good improvement in MEP was detected after three weeks of treatment protocol and was recorded both during rest (after-rest) and during activity (after-active) indicating restoration of contraction ability and thus making thumb useful.

FIG. 13 shows longitudinal electrophysiological changes recorded from the anterior deltoid muscle in the same Cr' subject of FIGS. 10-12. The deltoid muscle is the principle flexor muscle of the shoulder joints. The data shows the underlying mechanism of improvement in shoulder movement for this subject. The subject was evaluated 7 times (6 times during intervention and once four weeks after intervention. The strength of TMS pulse and the location of the stimulation was kept constant cross the evaluations.

Panel A shows examples of motor evoked potentials (MEPs) recorded before commencing the 6 week intervention (upper signal, blue) and during evaluation 7 (lower signal, red) four weeks after intervention ended. Note that these were recorded during an active condition in which the subject was holding the shoulder joint in flexion position against gravity.

A silent period (SP) is the flat portion of an MEP trace following the stimulus artifact in which muscle activity was absent (silent). In Panel A, a silent period is shown as the flat portion leading up to vertical line (blue) as obtained before the intervention commenced. The relatively longer flat trace leading up to vertical line (red) was recorded during evaluation 7, four weeks after the 6 week intervention had concluded. Substantially increased silent period is seen in the latter.

The increased duration of the silent period (red) indicates strengthening of cortical or/and spinal inhibitory mechanisms. The silent period is mediated by the neurotransmitter GABA at the cortical level, which is apparently enhanced here. Increased silent period might be the underlying mechanism leading to the reduction in spasticity and the better motor control that was demonstrated as a result of intervention for this CP subject. Panel D shows averages for silent periods for the 7 evaluations.

FIG. 13 panel B shows averages of MEPs during an active state in each evaluation for this CP subject. The bar graph shows the average and standard error of mean. The filled circles are individual data points (7 to 11 points from each recording session). FIG. 13 panel C shows averages of MEPs during rest state in which the subject was resting the shoulder.

The data indicates improved performance over course of intervention. Electrophysiological enhancements in motor activity evident at close of intervention were sustained at evaluation 7, four weeks after cessation of intervention.

FIG. 14 shows before and after treatment for a different CP subject. The dysfunctional right hand grip is demonstrated during peg-test task before treatment commenced. Significantly improved grasping capability is demonstrated after completion of 6 week intervention.

III. Subject with Stroke: N=1

Motor Skills: Peg-board time for this stroke subject was reduced from 103 to 77 seconds (25%).

Muscle strength: The table below shows changes in muscle strength from before to after 6 weeks treatment for a stroke subject. (Note that numbers are in pounds and changes therefore signify an enabling outcome.

| MMT | Left (before) (lbs) | Left After (lbs) |
|---|---|---|
| Shoulder Flexors | 14 | 23 |
| Shoulder Extensors | 28 | 33.5 |
| Shoulder Abductors | 5 | 17.5 |
| Shoulder IR | 0 | 27.5 |
| Shoulder ER | 0 | 20 |
| Elbow Flexion | 26 | 45 |
| Elbow Extension | 15 | 28.5 |
| Wrist Flexors | 10 | 15.5 |
| Wrist Extensors | 5 | 25 |
| Grip 1 | 11.8 | 19.7 |
| Grip 2 | 17.8 | 29.7 |
| Grip 3 | 18.5 | 31.8 |
| Grip 4 | 15.7 | 27.8 |
| Grip 5 | 14.1 | 24.3 |
| Pinch (key grip) | 14 | 16 |
| Pad-to-pad | 11.4 | 14.4 |
| Tip-to-tip | 6 | 9.2 |

Figures 15A, 15B:
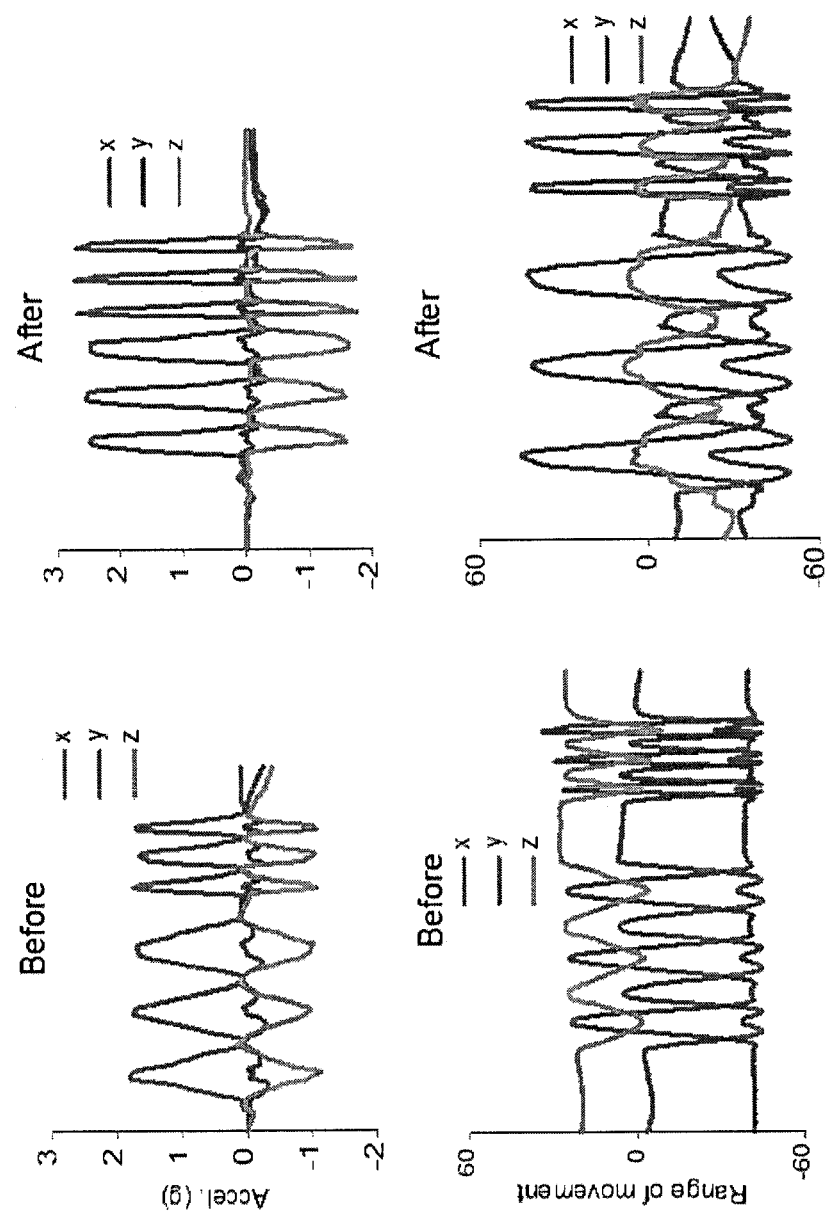
FIGS. 15A-B show, for a stroke subject, an improvement of 3D motion of the left elbow joint.

FIG. 15 shows, for this stroke subject, an improvement of 3D motion of the left elbow joint. Panel A, Before shows acceleration of the joint movement prior to Treatment, and After shows acceleration after treatment, where dexterity has returned. Panel B. Before The range of movement before treatment is compared to After showing substantially improved range of motion.

Systems

The present invention incorporates electrical and magnetic stimulator technology currently known in the art into novel and non-obvious commercially viable and meaningful embodiments. It will be appreciated that elements and components described herein may be further divided into additional components or joined together to form fewer components for performing the same functions in various practices of the invention. The following information is provided by way of illustration and not limitation:

Referring to FIG. 1, in the embodiment shown therein, stimulator 101 provides motor cortex stimulation. In embodiments of the invention: the first simulator 101 can be, for example, but is not limited to, a source of pulsed magnetic stimulation consistent with the disclosed practices herein, and which may be a private label stimulator with characteristics similar to a commercially available stimulator, such as a known Magstim Rapid2 magnetic stimulator which is a transcranial magnetic stimulation unit, for providing the desired pulsed magnetic stimulation, or alternatively a commercially available pulsed DC electric stimulator such as Digitimer D185 Multipulse stimulator, which is used for commonly transcranial stimulation, and may be used herein for pulsed motor cortex stimulation with standard commercially available Hydrogel electrodes from Axelgaard Manufacturing.

Stimulator 102 provides constant level continuous spinal stimulation at the spinal neural junction, which can be but is not limited to, trans-spinal direct current stimulation (tsDC), which can be provided by, for example, but is not limited to, a private label stimulator with characteristics similar to a commercially available stimulator, such as a Neuroconn DC-Stimulator, which can be used as a micro-processor-controlled constant current source, which provides a single channel, unipolar (DC) stimulation, with an adjustable range of current to 5,500 µA. Stimulator 102 applies constant current tsDC stimulation to the spine via a cathodal sponge electrode and the return electrode is also sponge, with conductive saline or gel.

Stimulator 103 provides stimulation of the peripheral nerves/muscles, which can be, for example, a source of pulsed DC stimulation consistent with the disclosed practices herein, and which may be a private label stimulator or a commercially available stimulator, such as a known. Digitimer D185 Multipulse Stimulator. In an exemplary embodiment, a Digitimer Stimulator DS7AH is used to stimulate either motor cortex or nerves at peripheral muscles along with standard commercially available Hydrogel electrodes from Axelgaard Manufacturing.

A system controller/synchronizer 104 is configured to control and synchronize the stimulation and in one embodiment can include a non-transitory computer usable medium (such as, but not limited to, RAM) 123. In some embodiments the system can include a channel amplifier 106, a data recorder 107 and a computer 108, where the computer is part of the system controller for stimulation, synchronization and data acquisition. MEPs are detected conventionally.

This disclosure includes description by way of example of a device configured to execute functions (hereinafter referred to as computing device) which may be used with the presently disclosed subject matter. The description of the various components of a computing device is not intended to represent any particular architecture or manner of interconnecting the components. Other systems that have fewer or more components may also be used with the disclosed subject matter. A communication device may constitute a form of a computing device and may at least include a computing device. The computing device may include an inter-connect (e.g., bus and system core logic), which can interconnect such components of a computing device to a data processing device, such as a processor(s) or microprocessor(s), or other form of partly or completely programmable or pre-programmed device, e.g., hard wired and or application specific integrated circuit ("ASIC") customized logic circuitry, such as a controller or microcontroller, a digital signal processor, or any other form of device that can fetch instructions, operate on pre-loaded/pre-programmed instructions, and/or followed instructions found in hard-wired or customized circuitry to carry out logic operations that, together, perform steps of and whole processes and functionalities as described in the present disclosure.

Each computer program may be implemented in any programming language, such as assembly language, machine language, a high-level procedural programming language, or an object-oriented programming language. The programming language may be a compiled or interpreted programming language.

Each computer program may be implemented in a computer program product tangibly embodied in a computer-readable storage device for execution by a computer processor. Method steps of the invention may be performed by a computer processor executing a program tangibly embodied on a computer-readable medium to perform functions of the invention by operating on input and generating output.

In this description, various functions, functionalities and/or operations may be described as being performed by or caused by software program code to simplify description. However, those skilled in the art will recognize what is meant by such expressions is that the functions result from execution of the program code/instructions by a computing device as described above, e.g., including a processor, such as a microprocessor, microcontroller, logic circuit or the like. Alternatively, or in combination, the functions and operations can be implemented using special purpose circuitry, with or without software instructions, such as using Application-Specific Integrated Circuit (ASIC) or Field-Programmable Gate Array (FPGA), which may be programmable, partly programmable or hard wired. The application specific integrated circuit ("ASIC") logic may be such as gate arrays or standard cells, or the like, implementing customized logic by metalization(s) interconnects of the base gate array ASIC architecture or selecting and providing metalization(s) interconnects between standard cell functional blocks included in a manufacturer's library of functional blocks, etc. Embodiments can thus be implemented using hardwired circuitry without program software code/instructions, or in combination with circuitry using programmed software code/instructions.

Thus, the techniques are limited neither to any specific combination of hardware circuitry and software, nor to any particular tangible source for the instructions executed by the data processor(s) within the computing device. While some embodiments can be implemented in fully functioning computers and computer systems, various embodiments are capable of being distributed as a computing device including, e.g., a variety of forms and capable of being applied regardless of the particular type of machine or tangible computer-readable media used to actually effect the performance of the functions and operations and/or the distribution of the performance of the functions, functionalities and/or operations.

The interconnect may connect the data processing device to define logic circuitry including memory. The interconnect may be internal to the data processing device, such as coupling a microprocessor to on-board cache memory or external (to the microprocessor) memory such as main memory, or a disk drive or external to the computing device, such as a remote memory, a disc farm or other mass storage device, etc. Commercially available microprocessors, one or more of Which could be a computing device or part of a computing device, include a PA-RISC series microprocessor from Hewlett-Packard Company, an 80×86 or Pentium® series microprocessor from Intel Corporation, a PowerPC® microprocessor from IBM, a SPARC microprocessor from Sun Microsystems, Inc, or a 68xxx series microprocessor from Motorola Corporation as examples.

The inter-connect in addition to interconnecting such as microprocessor(s) and memory may also interconnect such elements to a display controller and display device, and/or to other peripheral devices such as input/output (I/O) devices, e.g., through an input/output controller(s). Typical I/O devices can include a mouse, a keyboard(s), a modem(s), a network interface(s), printers, scanners, video cameras and other devices which are well known in the art. The interconnect may include one or more buses connected to one another through various bridges, controllers and/or adapters. In one embodiment the I/O controller includes a USB (Universal Serial Bus) adapter for controlling USB peripherals, and/or an IEEE-1394 bus adapter for controlling IEEE-1394 peripherals.

The memory may include any tangible computer-readable media, which may include but are not limited to recordable and non-recordable type media such as volatile and non-volatile memory devices, such as volatile RAM (Random Access Memory), typically implemented as dynamic RAM (DRAM) which requires power continually in order to refresh or maintain the data in the memory, and non-volatile RAM (Read Only Memory), and other types of non-volatile memory, such as a hard drive, flash memory, detachable memory stick, etc. Non-volatile memory typically may include a magnetic hard drive, a magnetic optical drive, or an optical drive (e.g., a DVD RAM, a CD RAM, a DVD or a CD), or 'other type of memory system which maintains data even after power is removed from the system.

For the purposes of describing and defining the present teachings, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

While the invention has been described in terms of specific embodiments, it is evident in view of the foregoing description that numerous alternatives, modifications and variations will be apparent to those skilled in the art. Accordingly, the invention is intended to encompass all such alternatives, modifications and variations which fall within the scope and spirit of the invention and the following claims,

The invention claimed is:

1. A system for improving neural communication impairment of a vertebrate being, the system comprising:
a first signal providing component configured to provide pulsed peripheral stimulation signals at a peripheral body part through a first signal transmission component for generating a first stimulation signal along a neural pathway;
a second signal providing component configured to provide a pulsed motor cortex stimulation signal to a motor cortex area through a second signal transmission component for generating a second stimulation signal along the neural pathway;
a DC signal providing component configured to provide a constant-level direct current spinal stimulation signal to a neural spinal, unction on the neural pathway; and
a controller component configured to control timing of the pulsed peripheral stimulation signals, the pulsed motor cortex stimulation signal, and the constant-level direct current spinal stimulation signal, for triple stimulation of the neural pathway by the pulsed peripheral stimulation signals, the pulsed motor cortex stimulation signal and the constant-level direct current spinal stimulation signal; where components of a neural pathway are reestablished by induced neural signals, which are generated by the pulsed peripheral stimulation signals, the puled motor cortex stimulation signal, and the constant-level direct current spinal stimulation signal.

2. The system of claim 1 wherein the DC signal providing component is also configured to provide a constant-level cathodal direct current spinal stimulation through an electrode.

3. The system of claim 2 wherein the electrode comprises a sponge electrode.

4. The system of claim 3 wherein a characteristic dimension of the sponge electrode is selected based on a predetermined current density.

5. The system of claim 1 wherein the second signal transmission component is a magnetic field producing component.

6. The system of claim 1 wherein the controller component is configured to provide, in sequence, a first peripheral stimulation pulse from the first signal providing component to stimulate a neural site of the peripheral body part and a subsequent second peripheral stimulation pulse to stimulate the neural site for generating a peripheral body part-issued stimulation signal on the neural pathway for stimulating the neural spinal junction during provision of the direct current spinal stimulation signal to the neural spinal junction, and a motor cortex stimulation pulse to stimulate the motor cortex for generating a motor cortex-issued stimulation signal for stimulating the neural spinal junction during provision of the direct current spinal stimulation signal to the neural spinal junction, for generating simultaneous triple stimulation of the neural spinal junction by the peripheral body part-issued stimulation signal, the motor cortex-issued stimulation signal and the direct current spinal stimulation signal.

7. The system of claim 6 wherein the controller component provides control of timing by applying the first peripheral stimulation pulse about 30 ms before the motor cortex pulse and applying the second peripheral stimulation pulse ranging between about 3 to about 12 ms before the motor cortex pulse.

8. The system of claim 7 wherein the DC signal providing component is configured to provide a constant-level cathodal direct current spinal stimulation signal at the neural spinal junction through a sponge electrode.

9. The system of claim 6 wherein the DC signal providing component is configured to provide a constant-level cathodal direct current spinal stimulation signal at the neural spinal junction through a sponge electrode.

10. A method for improving neural communication impairment of a vertebrate being, the method comprising:
providing pulsed peripheral stimulation signals at the peripheral body part through a first signal transmission component for generating a first stimulation signal along a neural pathway of the being;
providing a pulsed motor cortex stimulation signal to a motor cortex area through a second signal transmission component for generating a second stimulation signal along the neural pathway of the being;
providing a constant-level direct current spinal stimulation signal at a neural spinal junction; and
control timing of the pulsed peripheral stimulation signals and the pulsed motor cortex stimulation signal and the constant-level direct current spinal stimulation signal for triple stimulation of the neural pathway by the pulsed peripheral stimulation signals, the pulsed motor cortex stimulation signal and the constant-level direct current spinal stimulation signal; wherein components of a neural pathway are reestablished by induced neural signals, which are generated by the pulsed peripheral stimulation signals, the pulsed motor cortex stimulation signal, and the constant-level direct current spinal stimulation signal.

11. The method of claim 10 wherein the second signal transmission component is a magnetic field producing component.

12. The method of claim 10 further including the step of providing a constant-level cathodal direct current spinal stimulation signal at the neural spinal junction through an electrode.

13. The method of claim 12 wherein the electrode comprises a sponge electrode.

14. The method of claim 10 wherein controlling timing includes, in sequence, the steps of applying a first peripheral stimulation pulse to stimulate a neural site of the peripheral body part, and after first time delay applying a second peripheral stimulation mike to stimulate the neural site for generating a peripheral body-issued stimulation signal for stimulating the neural spinal junction during application of the direct current spinal stimulation signal to the spinal junction, and after a second time delay applying a motor cortex pulse to stimulate the motor cortex for generating a motor cortex-issued stimulation signal for stimulating the neural spinal junction during application of the constant-level direct current spinal stimulation signal, for simultaneous triple stimulation of the neural spinal junction.

15. The method of claim 14 wherein controlling timing includes, in sequence, the steps of applying the first peripheral stimulation pulse about 30 ms before the motor cortex pulse and applying the second peripheral stimulation pulse ranging between about 3 to about 12 ms before the motor cortex pulse.

16. The method of claim 14 wherein controlling timing further includes, in sequence, the steps of applying the first peripheral stimulation pulse about 30 ms before the motor cortex pulse and applying the second peripheral stimulation pulse ranging between about 3 to about 12 ms before the motor cortex pulse.

* * * * *

UNITED STATES PATENT AND TRADEMARK OFFICE
CERTIFICATE OF CORRECTION

PATENT NO.         : 9,008,781 B2                                    Page 1 of 1
APPLICATION NO.    : 14/201408
DATED              : April 14, 2015
INVENTOR(S)        : Ahmed et al.

It is certified that error appears in the above-identified patent and that said Letters Patent is hereby corrected as shown below:

Column 19, line 55 claim 1, "spinal, unction" should read -- spinal junction --

Column 19, line 65 claim 1, "signals, the puled" should read -- signals, the pulsed --

Column 21, line 14 claim 14, "stimulation mike" should read -- stimulation pulse --

Signed and Sealed this
First Day of March, 2016

Michelle K. Lee
*Director of the United States Patent and Trademark Office*